United States Patent [19]

Scholz, Jr.

[11] 4,229,168
[45] Oct. 21, 1980

[54] CONTRA-ANGLE ULTRASONIC ENDODONTIC INSTRUMENT

[76] Inventor: Howard W. Scholz, Jr., 1433 Monterey St., San Luis Obispo, Calif. 93401

[21] Appl. No.: 935,926

[22] Filed: Aug. 23, 1978

[51] Int. Cl.² .......................... A61C 1/07; A61C 3/03
[52] U.S. Cl. .................................... 433/124; 433/102
[58] Field of Search ............... 15/22 R; 128/755, 310; 32/58, 27; 433/124, 102

[56] References Cited

U.S. PATENT DOCUMENTS

| 3,368,280 | 2/1968 | Friedman et al. | 32/58 |
| 3,892,040 | 7/1975 | Marquis | 32/40 R |
| 3,969,823 | 7/1976 | Nakanishi | 32/58 |

Primary Examiner—Robert Peshock
Attorney, Agent, or Firm—Spensley, Horn, Jubas & Lubitz

[57] ABSTRACT

A contra-angle ultrasonic endodontic instrument is described which includes, basically, a head mechanically coupled to the ultrasonically driven shaft of an endodontic instrument. The head includes means, such as one or more holes, to receive a shaft of an endodontic tool of relatively uniform longitudinal and lateral cross-section with its longitudinal axis at a substantial angle to the longitudinal axis of the shaft, thus, ultrasonic vibrations in the shaft are transferred to the tool.

5 Claims, 3 Drawing Figures

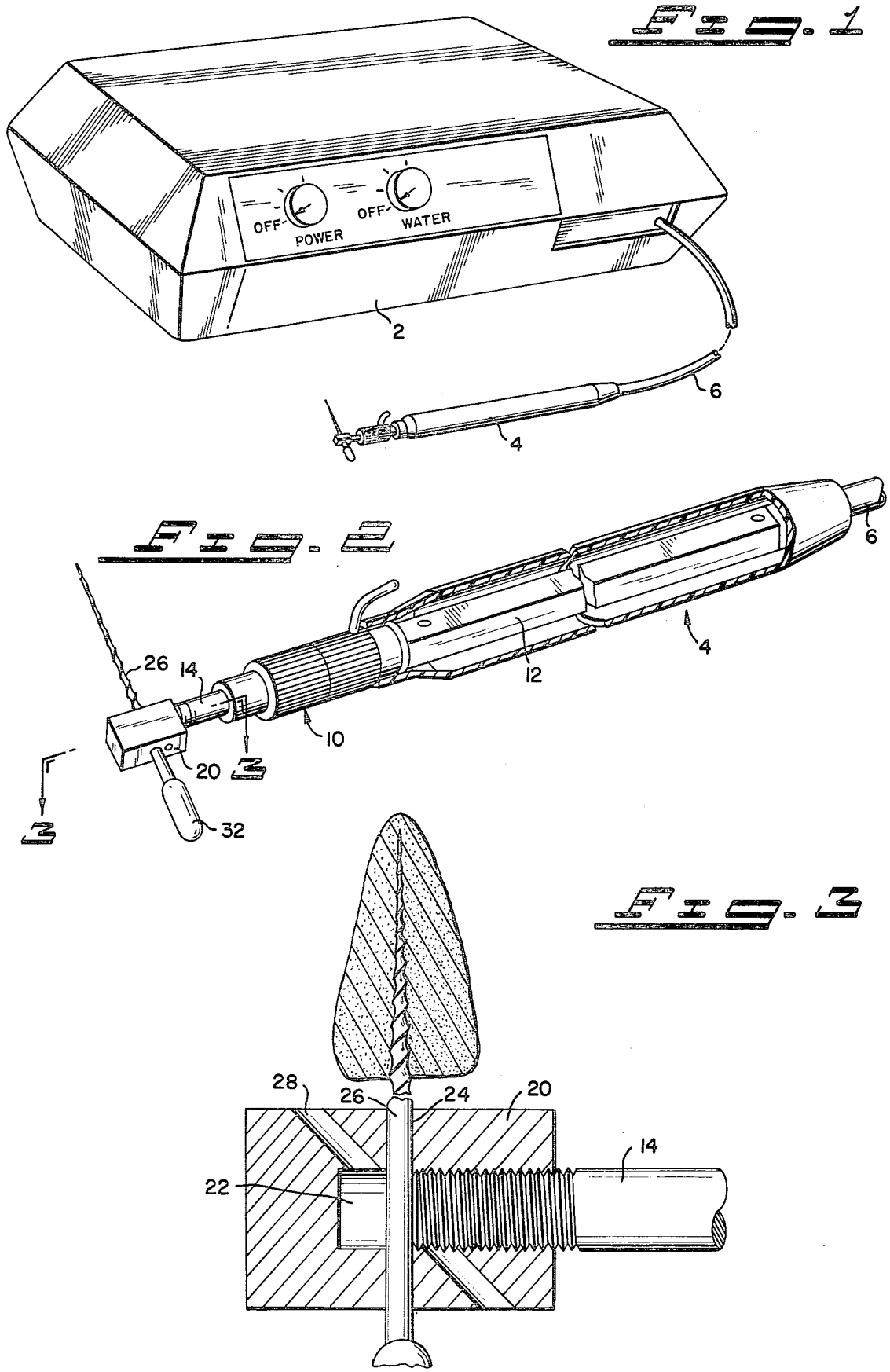

CONTRA-ANGLE ULTRASONIC ENDODONTIC INSTRUMENT

BACKGROUND OF THE INVENTION

The invention provides a contra-angle ultrasonic endodontic instrument.

In providing endodontic therapy, it is important for the dentist to completely clean all organic matter from the root canal of the tooth prior to filling it with medication or other material, otherwise inflammation and infection may result requiring the treatment to be repeated or the tooth to be removed. A typical theraputic approach followed at present requires the dentist to insert a narrow diameter file into the root canal sufficiently to reach the apex of the tooth, as measured on an X-ray, then to clean the root canal using this file and progressively larger files until only clean white dentin shavings are extracted with an irrigating solution. Since no satisfactory instrument at present exists to permit a dentist to perform endodontic operations on molars, in part because of their location and in part because of the complex shape of their root canals, for the most part such treatments are performed by hand. As a result, they are tiring, can prove quite difficult, and often result in incomplete or uneven removal of the nerve and pulp material, and bacteria. It would be most helpful to have an endodontic instrument capable of performing such treatments, particularly on molars for not only would such an instrument prove to be less tiring to the dentist but it also likely would result in improved cleansing of the root canal and therefore minimize inflamation and infection.

Various endodontic instruments have been designed; some of them have been patented. A recent endodontic instrument which is ultrasonically driven is being marketed by Cavitron, Inc. of Long Island City, N.Y. It is known as their Cavitron Ultrasonic Unit 1010 with a PR-30 ultrasonic insert. This insert includes, in addition to the ultrasonic driver, a shaft which transmits the ultrasonic vibrations through a block to an ultrasonic tool, the longitudinal axis of the tool being parallel to the longitudinal axis of the shaft. As a result, while this tool could be quite useful for performing endodontic treatments in teeth at the front of the patient's mouth, it is of limited usefulness for performing such treatments in molars. It would be highly desirable if the longitudinal axis of the endodontic tool were turned to lie at a substantial angle to the longitudinal axis of the shaft and instrument, and arrangement commonly termed a "contra-angle" instrument. It would also be highly desirable if such an instrument could be used in root canals of complex shapes.

The usefulness on a contra-angle instrument is well known; many such instruments have been designed and are in current use by dentists. Ultrasonic instruments also are well known. In view of these facts, it would seem to be a simple matter to provide a contra-angle, ultrasonic instrument for endodontic applications. While this objective certainly might be readily apparent to the designers of dental instruments, so far as is known, prior to this invention no such instrument has proven successfully for such application. The problem is a simple one. It is essential that the endodontic tool not break while in the root canal of a tooth. If it does, the dentist must spend a great deal of time trying to dislodge and work loose the broken tip. Often this effort is unsuccessful. At times, though, it is not. Ultrasonic instruments such as the Cavitron Ultrasonic Unit 1010 with the PR-30 insert are designed to transmit the major ultrasonic vibrations longitudinally through the shaft of the endodontic tool. As a result, when used in root canals of complex shape, they do not appear to produce, or result in, more than a normal number of tip breakage occurances during endodontic treatments. However, if the instrument is designed or modified so that the longitudinal axis of the endodontic tool lies at a substantial angle to the longitudinal axis of the shaft of the instrument, or if it is used in a root canal of complex shape, the ultrasonic vibrations apparently are transmitted with substantial transverse components to the endodontic tool. These transverse components appear to induce appreciable breakage of the tool resulting in a highly unsatisfactory instrument-at least that has been the experience of those instrument designers known to the present inventor. As a result, efforts to provide a contra-angle ultra sonic endodontic instrument largely have been abondoned in spite of the considerable appeal such as instrument would offer for endodontic work.

To understand the present invention, it is also important to know something about the various lines of endodontic tools. There are basically three types: broaches, reamers and files. All are tapered from a relatively large diameter base to a small diameter tip. A broach is a barbed tool; it has a number of leaves or barbs carved out of its sides which, upon drawing the tool out of the root canal, carve a portion out of the side of the canal. A Hedstrom file looks from the side like a number of cones with the apex of each stuck to the base of the next. Thus, neither a broach nor a Hedstrom file has a relatively uniform longitudinal and lateral cross-section. Both include areas or indentations laterally which substantially weaken the shaft. If lateral ultrasonic vibrations are transmitted to such shafts, they tend to break at such weakened areas. The reamer or file, however, is of relatively uniform longitudinal and lateral cross-section that is spiraled longitudinally. Some are of triangular cross-section; others have a square cross-section. Since they do not include laterally weakened areas, it has been found that ultrasonic vibrations with substantial lateral components can be imposed upon such endodontic reamers without tending to break them. Indeed, it has been found that such a reamer or file can be inserted into the complex, curved root canal of a molar, ultrasonic vibrations imparted to it with substantial lateral components, and the reamer or file used to perform endodontic treatments without experiencing any unusual number of tip breakages. Further, it has been found that should a tip break, another tool can be inserted into the root canal and its ultrasonic vibrations imparted to the broken tip through an irrigant or other fluid to quickly and easily float it free.

The present invention is based upon this important, new discovery.

BRIEF SUMMARY OF THE INVENTION

A contra-angle ultrasonic endodontic instrument is set forth which incorporates an ultrasonic vibration generator and means for actuating the generator to produce mainly longitudinal vibrations. A shaft is mechanically coupled to the ultrasonic generator to vibrate along its longitudinal axis. Means are provided for mechanically coupling an endodontic tool of relatively uniform longitudinal and lateral cross-section to the outer tip of the shaft with the longitudinal axis of the tool at a substantial angle to the longitudinal axis of the shaft so that the ultrasonic vibrations in the shaft are transmitted to the tool. Preferably the means for mechanically coupling the endodonic tool to the shaft include a head that is threadably connected to the shaft, the head including one or more transverse holes for receiving a shaft of a tool. Also, preferably means are provided to removably secure the tool, head and shaft assembly together. These and other features of the invention will be set forth in the following description of a preferred embodiment.

BRIEF DESCRIPTION OF DRAWINGS:

The invention will be further described in connection with the accompanying drawings, in which:

FIG. 1 is a perspective view of an ultrasonic unit incorporating a contra-angle ultrasonic endodontic instrument;

FIG. 2 is an enlarged view of the conta-angle ultrasonic endodonic instrument, partially broken away; and FIG. 3 is an enlarged view, partially in cross-section, of the tip of the contra-angle ultrasonic endodontic instrument taken generally as line 3—3 of FIG. 2 and showing a portion of the tool received in the root canal of a tooth.

DETAILED DESCRIPTION

The design principles set forth herein for a contra-angle ultrasonic endodonic instrument can, of course, be applied to any of a variety of ultrasonic instruments. An ultrasonic instrument in wide use today by dentists is the Ultrasonic Unit 1010 manufactured and marketed by Cavtron, Inc. of Long Island City, N.Y. In FIG. 1 is shown the general outlines of such a unit 2 which drives an instrument 4 through a cord 6.

The instrument itself is shown in FIG. 2 enlarged and partially in section. It includes an insert 10 that incorporates an ultrasonic driver 12 and a shaft 14. The ultrasonic driver 12 basically consists of a series of elements, or stacks, which upon application of an electric potential change their longitudinal dimension. This electric potential, and a cooling liquid for the stacks, is applied by the unit to the instrument through cord 6. The instrument shown is generally the PR-30 Cavitron instrument. One characteristic of this particular head is that both longitudinal and lateral vibrations are simultaneously generated, resulting in an eliptical motion of shaft 14. These vibrations are transmitted to shaft 14.

A head 20 is mechanically coupled to shaft 14. Preferably, as best shown in FIG. 3, head 20 includes a blind cylindrical hole 22 that is threaded to receive the threaded outer end of shaft 14. Head 20 also includes one or more holes 24 to receive the shaft of and endodonic tool 26. Preferably the longitudinal axis of one such hole 24 is generally at right angles to the longitudinal axis of shaft 14 while another such hole, 26', may be provided with its longitudinal axis at some other angle to the longitudinal axis of the shaft, such as at a 45 degree angle. Thus, the endodontic tool may be received within head 20 either at right angles to shaft 14 or at some other substantial angle to shaft 14. By simply twisting the head, it and the tool may be firmly secured on shaft 14 to prevent the ultrasonic vibrations from loosening the threaded connection of shaft 14 and head 20 during an endodontic treatment. Of course, a variety of other designs for attaching the shaft, head and tool to one another could be provided.

While the endodontic tool 26 is shown as including a bulbous base 32 typical of hand-held endodontic tools, this base may be removed or the shaft may terminate in a base end of a cross-sectional dimension comparable to the mid-section of the shaft if desired.

It is important that the endodontic tool not include chips, nicks, or other indentations which might substantially weaken it laterally. In other words, the tool should have a relatively uniform longitudinal and lateral cross-section. Among such tools which have been found to operate satisfactorily in this conta-angle ultrasonic endodontic instrument are reamers, files, reamers and file blanks, stocks, hand condensors or pluggers, orthodontic wire, and silver points, as contrasted with broaches and Hedstrom files both of which include indentations which substantially weaken them laterally.

In use, it has been found that the disclosed endodontic instrument performs quite satisfactorily, cleaning the root canal of organic matter relatively simply and easily. Examination of the resulting enlargement of the root canal has shown it to be exceptionally free of organic matter when compared with the enlarged root canal of a tooth cleaned by hand employing typical endodontic tools and techniques. Also, it has been found that the instrument achieves this important result without appreciable effort by the dentist, as contrasted with the considerable effort often required to clean and prepare a root canal by hand. Further, it has been found that should the tip of the endodontic tool break and lodge within the root canal, it may be floated free in a relatively easy and simple fashion by inserting the ultrasonically driven endodontic tool into the root canal flooded with an irrigating solution, the tool applying ultrasonic vibrations through the solution to the broken tip causing it to vibrate and float free. Similarly, silver points previously inserted in the root canal easily can be freed and removed using this unique instrument. Further, the instrument can be used to fill a cleansed root canal with any of the various endodontic materials normally used, such as root canal sealers, gutta percha, and various medications. For these and other reasons, the disclosed instrument is believed to offer highly important and significant advantages for endodontic treatments.

As described in the thesis by the inventor titled "Ultra sonic Versus Hand Filing of the Human Root Canal System" and submitted to the Loma Linda University Graduate School in partial fulfillment of his requirements for the degree of Master of Science in the field of endodontics, it is preferred that the instrument be employed with K-type stainless steel files to clean the root canal, the canal being flooded throughout the cleansing operation with a 10 per-cent aqueous solution of ethylenediamine tetraacetic acid (EDTA) with benzalkonium chloride at a concentration of 1:3,000. This was found to result in a root canal of significantly improved cleanliness when compared, under examination using a scanning electron microscope, to one prepared by conventional techniques and using a conventional irrigating solution. Apparently, among other things the ultrasonic vibrations significantly increase the bactericidal effect of antibacterial agents such as benzalkonium chloride.

While a preferred embodiment of the invention has been disclosed, it will be apparent to those skilled in this field that various other embodiments of the invention could be designed using the teaching herein set forth. Accordingly, the scope of the invention is not limited to the preferred embodiment herein described, but rather are set forth in the following claims.

I claim the right to exclude others from making, using or selling:

1. A contra-angle ultrasonic endodontic instrument including:
   ultrasonic vibration generator means for simultaneously producing both longitudinal and lateral ultrasonic vibrations;
   means for actuating the ultrasonic generator means to produce vibrations;
   a shaft mechanically coupled to the ultrasonic generator means to vibrate both longitudinal and laterally along its main longitudinal axis;
   an endodontic tool of relatively uniform longitudinal and lateral cross-section that is spiraled longitudinally and that is free of indentations along its length; and
   means for mechanically coupling the endodontic tool to the shaft with the longitudinal axis of the tool at a substantial angle to the longitudinal axis of the shaft so that the ultrasonic vibrations in the shaft are transmitted to the tool.

2. A contra-angle ultrasonic endodontic instrument as set forth in claim 1 in which the means to couple the endodontic tool to the shaft includes a head, and means attaching the head to the shaft, the head including a transverse hole for receiving the shaft of an endodontic tool.

3. A contra-angle ultrasonic endodontic instrument as set forth in claim 2 in which the means to mechanically couple the assembly includes a threaded shaft, the head having an internally threaded opening, the head being threaded onto the shaft sufficiently to cause the end of the shaft to bear against the side of the endodontic tool received in the transverse hole in the head, and to thereby hold the assembly together.

4. A contra-angle ultrasonic endodontic instrument as set forth in claim 2 in which the head includes a plurality of holes for receiving the tool at any of various different angles to the longitudinal axis of the shaft.

5. A contra-angle ultrasonic endodontic instrument as set forth in claim 2 in which the endodontic tool is selected from the group consisting of reamers, files, reamers and file blanks, stock, hand condensors or pluggers, orthodontic wire, and silver points.

* * * * *